United States Patent [19]

Tan et al.

[11] Patent Number: 5,233,073
[45] Date of Patent: Aug. 3, 1993

[54] SECONDARY AMINES CONTAINING NADIC AND BENZOCYCLOBUTENYL GROUPS

[75] Inventors: Loon-Seng Tan; Fred E. Arnold, both of Centerville, Ohio

[73] Assignee: The United States of America as represented by the Secretary of the Air Force, Washington, D.C.

[21] Appl. No.: 854,727

[22] Filed: Mar. 23, 1992

[51] Int. Cl.$^5$ ............... C07C 255/50; C07C 233/18; C07C 211/27
[52] U.S. Cl. ................................ 558/424; 564/219; 564/389
[58] Field of Search ............... 558/424; 564/219, 389

[56] References Cited

U.S. PATENT DOCUMENTS

| | | | |
|---|---|---|---|
| 3,784,642 | 1/1974 | Jenny et al. | 564/219 |
| 5,041,604 | 8/1991 | Saito et al. | 558/424 |

OTHER PUBLICATIONS

Chemical Abstracts, vol. 115, No. 22, Abst. 233,529 (1991).
Tan et al., *Polymer Preprints* 1991, vol. 32(1), pp. 636–637.

*Primary Examiner*—Joseph Paul Brust
*Assistant Examiner*—Mary Susan H. Gabilan
*Attorney, Agent, or Firm*—Charles E. Bricker; Donald J. Singer

[57] ABSTRACT

Provided are the dialkyl amines:

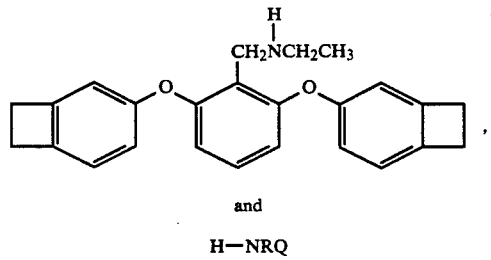

and

H—NRQ wherein Q is

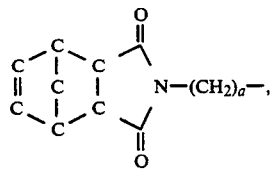

R is —CH$_3$ or Q and a has a value of 1 to 3.

4 Claims, No Drawings

1

SECONDARY AMINES CONTAINING NADIC AND BENZOCYCLOBUTENYL GROUPS

RIGHTS OF THE GOVERNMENT

The invention described herein may be manufactured and used by or for the Government of the United States for all governmental purposes without the payment of any royalty.

BACKGROUND OF THE INVENTION

This invention relates to reactive secondary amino compounds.

Chopped fiber reinforced plastics are currently being used in the fabrication of a wide variety of components. There are several disadvantages in the use of fiber for the reinforcement of plastic. In the case of chopped glass fibers, a large amount of fiber, generally a minimum of 30 percent by weight, is necessary for reinforcement because of the low reinforcing effect of the fiber. There is a practical processing limit on the effective fiber length. A macroscopically long fiber length is required with due regard for breaking or destruction of the fiber during processing, particularly molding. Composite materials containing chopped fibers are generally less processable than their non-reinforced counterparts. The shape of moldings is often limited to simple block or sheet forms. Films or filaments cannot be formed from chopped glass fiber-reinforced plastics. Other disadvantages of these materials include poor surface properties of molded articles, an anisotropy in dynamic properties, molding defects due to heterogeniety of the polymeric materials, and low cycle time in processing.

A need exists for high strength reinforced composites and a method for their manufacture which possess at least the following desirable prerequisites: (1) non-reliance on fiber reinforcement for the attainment of high strength properties; (2) circumvention of the complexities of current composite fabrication procedures; and (3) elimination of any possibility of fiber-polymer interface problems.

Various attempts have been made to overcome some of the above-described disadvantages of chopped-fiber reinforced plastics. One approach described by Helminiak et al, U.S. Pat. Nos. 4,207,407 and 4,377,546, comprises the dispersion of an intrinsically rigid rod-like heterocyclic polymer in a flexible, coil-like heterocyclic polymer.

The above composites are referred to as molecular composites. While this approach represents a valuable contribution to the art, it has certain drawbacks. For example, poly(p-phenylene benzobisthiazole) (PBT) has superior mechanical properties and thermal stability. However, PBT degrades before it melts; therefore, processing of a composite containing PBT must be carried out in a solution state with an acid, such as methanesulfonic acid (MSA), as the solvent. Relatively few flexible coil polymers can be dissolved in or are stable in MSA, thus limiting the choice of matrix polymers. Molecular composites based on PBT and poly-2,5-benzimidazole (ABPBI) have been fabricated into fibers and thin films. However, ABPBI does not have a glass transition temperature ($T_g$). Therefore, molecular composites containing ABPBI are difficult to thermally consolidate into thicker specimens. To overcome this problem, thermoplastic matrices have been used so that the molecular composite films could be laminated. However, thicker specimens fabricated using thermoplastic matrices are limited to use at temperatures below the $T_g$ of the matrix polymer(s). Conventional thermoset resins, such as bismaleimides, epoxies and the like, are not stable in the acid medium used to process the rigid-rod polymer, and cannot be used as host matrices for molecular composites.

A drawback to molecular compositions based upon rod-like and coil-like aromatic heterocyclic polymers has to do with phase separation between the two polymers. Such separation can occur during coagulation/precipitation and/or during consolidation. During coagulation/precipitation the polymers can separate due to insufficient entanglement on the part of the coil-like polymer, lack of strong rod-coil specific interaction or differences in rates of coagulation. Phase separation can also be thermally induced during consolidation.

One solution to the problem of phase separation is provided by Tan et al, U.S. Pat. No. 5,086,120 which discloses a molecular composite system consisting essentially of a para-oriented benzobisazole polymer and poly(2-acrylamido-2-methylpropanesulfonic acid). This molecular composite system can be processed into fibers and films with little or no detectable phase separation.

A drawback to molecular composites based upon rod-like aromatic heterocyclic polymers and thermoplastic or thermosetting resins has to do with the propensity of the rod-like materials to agglomerate. Serious agglomeration can lead to structural failure. Minor agglomeration can often be accomodated. What is desired is a molecular composite system in which there is interaction between the matrix polymer and the rod-like polymer sufficient to overcome any tendency toward phase separation.

Another solution to the problem of phase separation is provided by co-pending application Ser. No. 07/854,732, filed of even date, in which there is described a polymer which can undergo thermally-induced transformation to provide a reinforcing component and a matrix component. Preparation of the polymer is based, in part, on the novel amines described hereinafter.

Accordingly, it is an object of this invention to provide novel amino compounds.

Other objects, aspects and advantages of the present invention will become apparent to those skilled in the art from a reading of the following detailed description of the invention.

SUMMARY OF THE INVENTION

In accordance with the present invention, there are provided the dialkyl amines:

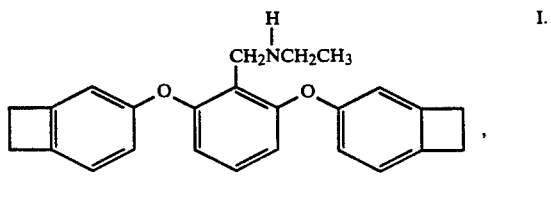

I.

and

H—NRQ    II.

wherein Q is

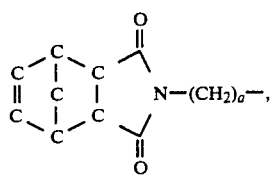

R is —CH₃ or Q and a has a value of 1 to 3.

N-ethyl-(2,6-di-benzocyclobutenoxy)benzylamine (I) is prepared as shown in the following sequence of reactions:

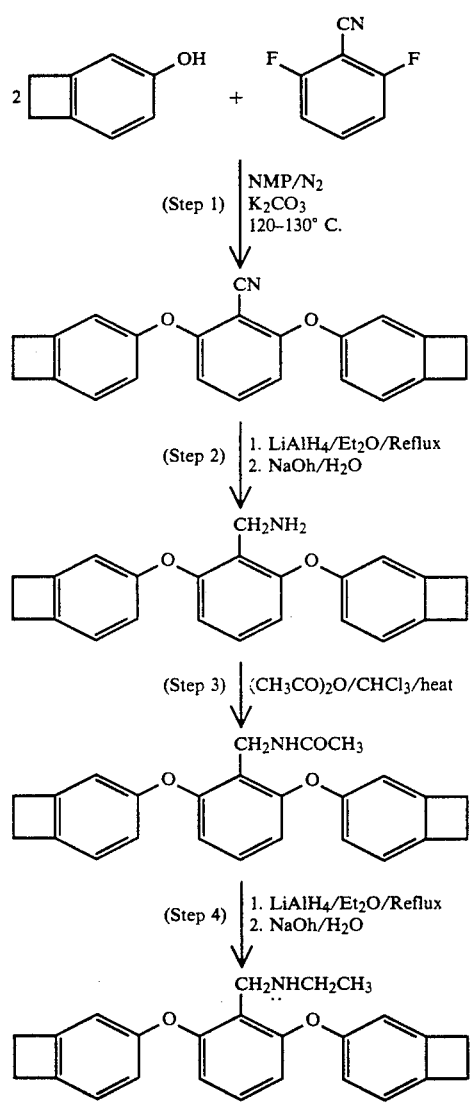

In the first step, 2,6-difluorobenzonitrile is reacted with 4-hydroxybenzocyclobutene in the presence of a large excess of potassium carbonate in N-methylpyrrolidinone (NMP) at 120°-130° C. leading to the formation of 2,6-di-(4-hydroxybenzocyclobutenyl)benzonitrile. Reduction of the latter (step 2) using lithium aluminum hydride in refluxing ether, followed by an alkaline quench, provides the corresponding benzylamine. Acetylation of the benzylamine in refluxing chloroform (step 3), followed by recrystallization from a suitable solvent affords the corresponding amide. Reduction of the latter (step 4) using lithium aluminum hydride in refluxing ether, followed by an alkaline quench, provides the desired amine, I.

The nadic amine (II) is prepared by refluxing the appropriate amine with nadic anhydride as shown in the following reactions:

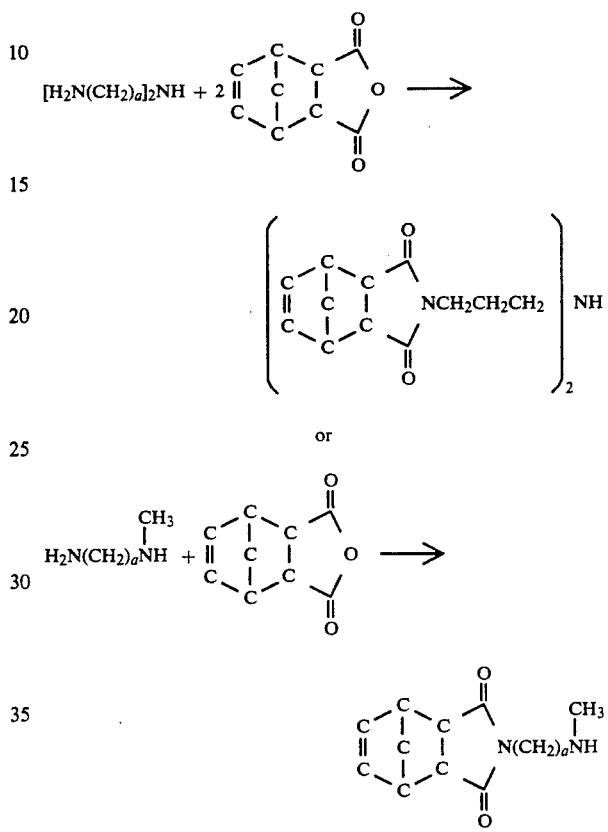

The polymer mentioned previously has repeating units of the formula:

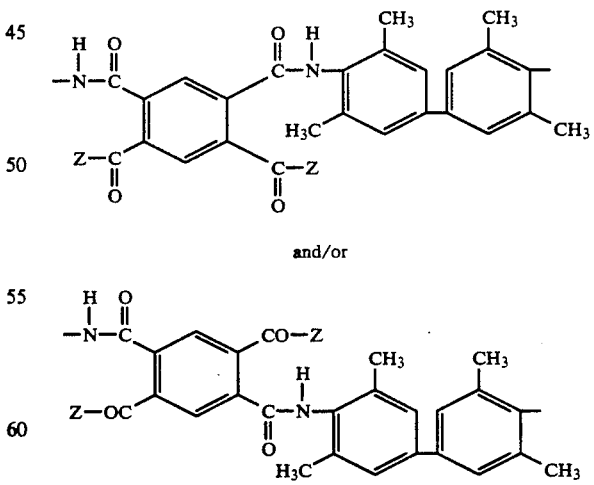

wherein Z is one of the dialkyl amino moieties set forth above. This polymer is what may be called a precursor polymer. When heated to a suitable temperature, it undergoes imidization to provide the rigid rod polymer poly(4,4'-biphenyl pyromellitimide):

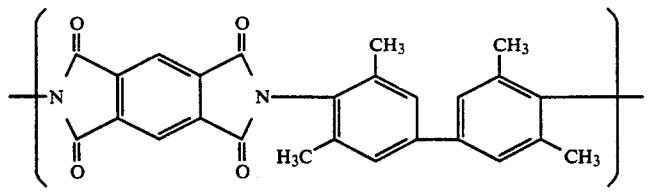

and 2 Z moieties per repeating unit. These Z moieties contain reactive groups which can undergo insitu addition reaction to form a thermoset matrix.

The following examples illustrate the invention.

EXAMPLE I

Preparation of iminobis(N-propylnadic imide) (DNI-3A)

9.00 g (54.82 mmol) of nadic anhydride (cis-5-norbornene-endo-2,3-dicarboxylic anhydride) was dissolved in 60 ml of chloroform in a 250 ml round-bottomed flask. 3.5 g (26.65 mmol) of 3,3'-iminobispropylamine was mixed with 40 ml of chloroform in a pressure-equalizing addition funnel. The latter solution was added dropwise to the nadic anhydride/chloroform solution with rapid stirring over a period of 30 minutes. A white precipitate formed with a slight exotherm. After addition was complete, the addition funnel was replaced with a reflux condensor and the mixture was heated to reflux. The reaction mixture was refluxed overnight. After cooling to room temperature, the mixture was poured into a separation symbol containing 300 ml distilled water. The bottom layer was collected and dried over anhydrous $MgSO_4$. Solvent was removed from the crude product by rotary evaporation. The product was dried in vacuo at 50° C. for 30 hours. Yield, 10.0 g (89%). Analysis calculated for $C_{24}H_{29}N_3O_4$: C, 68.06; H, 6.90; N, 9.92. Found: C, 67.98; H, 6.87; N, 9.80.

The thermal properties of the dinadic imide were determined by differential scanning calorimetry (DSC) and thermogravimetric analysis (TGA). When the imide was subjected to DSC analysis at normal pressure, under $N_2$, its melting endotherm was observed at 92° C. (maximum), followed by an endotherm attributable to the volatilization of the product. When the DSC run was conducted under 750 psi nitrogen pressure, a curing exotherm was observed with onset temperature at 221° C. and maximum temperature at 272° C. TGA of the product in air indicated the onset of decomposition at 229° C.

EXAMPLE II

Preparation of N-ethyl-(2,6-di-benzocyclobutenoxy) benzylamine (EBA-BCB)

2,6-di-(4-benzocyclobutenoxy)benzonitrile 3.85 g (27.68 mmol) of 2,6-difluorobenzonitrile, 8.00 g (57.88 mmol) anhydrous potassium carbonate and 7.50 g (62.42 mmol) 4-hydroxybenzocyclobutene were placed in a 250 ml, 3-necked round-bottomed flask equipped with a Dean-Stark trap, reflux condensor, nitrogen adapter, overhead mechanical stirrer and a thermometer adapter. To this mixture were added 120 ml of N-methylpyrrolidione (NMP) and 80 ml dry toluene. The resulting reaction mixture was stirred vigorously and heated rapidly in an oil bath under a nitrogen blanket. The internal temperature of the reaction mixture was maintained at about 120° C. for 48 hours. The resulting mixture was dark with a precipitated solid forming a ring on the walls of the flask just above the surface of the solution.

After the reaction mixture had cooled to room temperature, it was filtered and the reaction vessel was rinsed with methylene chloride. The combined filtrate was transferred to a 500 ml round-bottomed flask and subjected to rotary evaporation to remove the methylene chloride and toluene. The remaining dark liquid was poured into a stirred, cold aqueous HCl solution (100 ml conc. HCl + 1400 ml distilled water). A brown precipitate formed. This precipitate was allowed to stand at room temperature for several hours, then collected by vacuum filtration and washed with water until the filtrate was neutral to litmus paper. The crude produce was air-dried under suction overnight, then redissolved in about 200 ml of methylene chloride. The resulting solution was dried over anhydrous $MgSO_4$ and filtered. The filtrate was subjected to rotary evaporation. After the volume of filtrate had been reduced to about 50 ml, 100 ml of hexane was added. Rotary evaporation was continued to completely remove the solvents. About 9.15 g of crude product was obtained.

The crude product was dissolved in about 100 ml of ethyl acetate and the resulting solution was passed through a silica gel column, eluting with 1:4 ethyl acetate/hexane. The first fraction was collected and complete removal of the solvent via rotary evaporation led to the isolation of the desired product. Yield: 8.70 g (93%).

Analysis calculated for $C_{23}H_{17}NO_2$: C, 81.39; H, 5.05; N, 4.14. Found: C, 80.88; H, 5.14; N, 3.90.

Mass Spectral Analysis: $M^+ = 339$ (relative abundance of 19.25%).

IR (KBr, band frequency in $cm^{-1}$): 2830 w, 2868 vw, (CH stretch); 2228 m (C≡N stretch); 1215 vs (Ar-O-Ar stretch).

$^1$HNMR ($CDCl_3$.δ in ppm, TMS as internal standard).

2,6-di-(4-benzocyclobutenoxy)benzylamine

In a 500 ml, 4-necked round-bottomed flask equipped with an overhead mechanical stirrer, a thermometer/adaptor, a reflux condensor and a funnel was added 2,6-di-(4-benzocyclobutenoxy)benzonitrile followed by 260 ml of anhydrous diethyl ether. The resultant mixture was placed in an ice bath and stirred under a nitrogen atmosphere. When the internal temperature reached 0° C., lithium aluminum hydride was added through the attached funnel in 3 portions (0.69 g, 0.96 g, 0.50 g), each addition followed by washing the funnel with about 10 ml $Et_2O$, over a period of 15 minutes. The resulting mixture was stirred at 0° C. for 20 minutes, then the ice bath was removed and the mixture. was allowed to warm to room temperature. The reaction mixture was then refluxed gently for 17 hours.

The reaction mixture was then chilled in an ice bath, then quenched with 5 ml of distilled water, 2.5 ml 20%

NaOH and 16 ml distilled water. Internal temperature was maintained at 0° to 5° C. during quenching. The ice bath was removed and the mixture was allowed to warm to room temperature. The mixture was filtered and the residue was washed with Et$_2$O. About 400 ml of greenish yellow filtrate was dried over anhydrous MgSO$_4$, then gravity filtered into a flask. Removal of the ether yielded 7.25 g (97%) of a viscous amber liquid.

Analysis calculated for C$_{23}$H$_{21}$NO$_2$: C, 80.44; H, 6.16; N, 4.08. Found: C, 79.77; H, 6.08; N, 3.92.

Mass Spectral Analysis: M$^+$=343 (relative abundance of 16.68%); (M-NH$_3$)$^+$=326 (relative abundance of 100%).

IR (KBr, band frequency in cm$^{-1}$): 3383 vw, 3296 (NH$_2$ stretches); 3013 w, 3049 w, 3074 w (aromatic CH stretches); 2830 m, 2864 m, 2925 s, 2964 ms (aliphatic CH stretches); 1236 vs, 1221 vs (Ar-O-Ar stretches).

$^1$HNMR (CDCl$_3$. $\delta$ in ppm, TMS as internal standard): 1.70 (singlet, 2H, NH$_2$), 3.18 (singlet, 8H, alicyclic protons), 3.99 (singlet, 2H, benzyl protons), 6.57-7.58 (multiplets, 9H, aromatic protons).

N-[2,6-di-(4-benzocyclobutenoxy)]benzyl acetamide 7.00 g (20.38 mmol) of 2,6-di-(4-benzocyclobutenoxy)benzylamine and 60 ml chloroform were placed in a 250 ml round-bottomed flask. To the resulting amber solution was added, in portions and at room temperature, a solution of 2.60 g (25.47 mmol) acetic anhydride, 2.02 g (25.57 mmol) pyridine and 10 ml chloroform. The reaction was instantaneous and exothermic, as evidenced by self-refluxing of the chloroform. After completion of the addition, the solution was gently refluxed overnight. The reaction mixture was poured into a 1 l separatory funnel containing 350 ml distilled water. After shaking the mixture vigorously, the chloroform (bottom) layer was collected. The chloroform layer was washed twice more, then collected and dried over anhydrous MgSO$_4$. Removal of the chloroform yielded 7.70 g of off-white crude product. Recrystallization of the crude product from methanol/hexane (v/v, 1:25) yielded 6.20 g (79%).

Analysis calculated for C$_{25}$H$_{23}$NO$_3$: C, 77.90; H, 6.01; N, 3.63. Found: C, 77.26; h, 6.14; N, 3.29.

Mass Spectral Analysis: M$^+$=385 (relative abundance of 17.49%); (M-CH$_3$CONH$_2$)$^+$=326 (relative abundance of 96.09%).

IR (KBr, band frequency in cm$^{-1}$): 3281 s (NH stretch); 3060 w (aromatic CH stretches); 2826 w, 2930 m, 2975 m (aliphatic CH stretches); 1641 vs (amide carbonyl stretch); 1240 ms, 1227 v (Ar-O-Ar stretches).

$^1$HNMR (CDCl$_3$.$\delta$ in ppm, TMS as internal standard): 1.90 (singlet, 3H, CH$_3$), 3.20 (singlet, 8H, alicyclic protons), 4.69 (doublet, 2H, benzyl protons), 5.90 (broad, NH), 6.53-7.36 (multiplets, 9H, aromatic protons).

N-ethyl-(2,6-di-benzocyclobutenoxy)benzylamine 5.50 g (14.27 mmol) of N-[2,6-di-(4-benzocyclobutenoxy)]benzyl acetamide and 250 ml anhydrous diethyl ether were placed in a 500 ml, 4-necked round bottomed flask. The flask was placed in an ice bath and the mixture stirred under a N$_2$ atmosphere. When the internal temperature reached 0° C., LiAlH$_4$ was added in two portions, 0.73 g and 0.92 g. The resulting mixture was stirred at 0° C. for 20 minutes, then the ice bath was removed to allow the mixture to warm to room temperature. The reaction mixture was then refluxed for 17 hours.

The reaction mixture was chilled in an ice bath, then quenched, sequentially, with 3.5 ml distilled water, 1.65 ml 20% NaOH and 9 ml distilled water. The reaction mixture was maintained at 0° to 5° C. during quenching. The ice bath was removed to allow the mixture to warm to room temperature, then filtered. The filtrate was dried over anhydrous MgSO$_4$. The Et$_2$O was removed by rotary evaporation. Product yield: 4.15 g (97%).

Analysis calculated for C$_{23}$H$_{25}$NO$_2$: C, 80.83; H, 6.78; N, 3.77. Found: C, 80.56; h, 6.75; N, 3.54.

Mass Spectral Analysis: M$^+$=371 (relative abundance of 47.12%); (M-NHCH$_2$CH$_3$)$^+$=327 (relative abundance of 17.68%).

IR (KBr, band frequency in cm$^{-1}$): 3337 vw (NH stretch); 2828 ms, 2863 vw, 2926 ms, 2967 ms (CH stretch); 1227 vs (Ar-O-Ar stretch).

$^1$HNMR (CDCl$_3$.$\delta$ in ppm, TMS as internal standard): 1.10 (triplet, 3H, CH$_3$), 1.96 (singlet, NH), 2.72 (quartet, 2H, CH$_2$), 3.17 (singlet, 8H, alicyclic symbols), 3.99 (singlet, 2H, benzyl protons), 5.90 (broad, NH), 6.53-7.33 (multiplets, 9H, aromatic protons).

DSC of the product exhibited a first curing exotherm with onset at 225° C., maximum at 258° C., T$_g$ 137° C., and a second curing exotherm with onset at 327° and maximum at 357° C. TGA in air exhibited 16% weight loss in the range 222°-262° C., 30% weight loss in the range 419°-452° C. and 50% weight loss in the range 511°-543° C.

Various modifications may be made to the invention as described without departing from the spirit of the invention or the scope of the appended claims.

We claim:
1. N-ethyl-(2,6-di-benzocyclobutenoxy)benzylamine.
2. 2,6-di-(4-benzocyclobutenoxy)benzonitrile.
3. 2,6-di-(4-benzocyclobutenoxy)benzylamine.
4. N-[2,6-di-(4-benzocyclobutenoxy)]benzyl acetamide.

* * * * *